(12) United States Patent
Shimko et al.

(10) Patent No.: US 8,317,792 B2
(45) Date of Patent: Nov. 27, 2012

(54) OSTEOCHONDRAL IMPLANT FIXATION METHOD

(75) Inventors: Daniel Andrew Shimko, Germantown, TN (US); Jeetendra Subhash Bharadwaj, Memphis, TN (US); Carlos E. Gil, Collierville, TN (US); Eric D. Weeks, Millington, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 126 days.

(21) Appl. No.: 12/757,410

(22) Filed: Apr. 9, 2010

(65) Prior Publication Data

US 2010/0198223 A1   Aug. 5, 2010

Related U.S. Application Data

(62) Division of application No. 11/340,884, filed on Jan. 27, 2006, now Pat. No. 7,722,614.

(51) Int. Cl.
*A61B 17/16* (2006.01)
(52) U.S. Cl. ............................................. 606/79; 606/96
(58) Field of Classification Search .............. 606/79–81, 606/86 R, 87, 88, 96
See application file for complete search history.

(56) References Cited

U.S. PATENT DOCUMENTS

| | | | |
|---|---|---|---|
| 4,649,918 A | | 3/1987 | Pegg et al. |
| 5,320,115 A | | 6/1994 | Kenna |
| 5,632,745 A | * | 5/1997 | Schwartz ........................ 606/75 |
| 5,827,199 A | | 10/1998 | Alexander |
| 5,919,196 A | * | 7/1999 | Bobic et al. .................. 606/86 R |
| 6,375,658 B1 | | 4/2002 | Hangody et al. |
| 6,520,964 B2 | | 2/2003 | Tallarida et al. |
| 7,087,082 B2 | | 8/2006 | Paul et al. |
| 7,264,634 B2 | | 9/2007 | Schmieding |
| 7,510,558 B2 | | 3/2009 | Tallarida et al. |
| 2001/0039455 A1 | | 11/2001 | Simon et al. |
| 2002/0198479 A1 | | 12/2002 | Talish |
| 2003/0135209 A1 | | 7/2003 | Seedhom et al. |
| 2004/0148030 A1 | | 7/2004 | Ek |
| 2004/0230303 A1 | | 11/2004 | Gomes et al. |
| 2005/0222687 A1 | | 10/2005 | Vunjak-Novakovic et al. |
| 2005/0251268 A1 | | 11/2005 | Truncale |
| 2006/0247790 A1 | * | 11/2006 | McKay ..................... 623/23.44 |
| 2007/0083268 A1 | | 4/2007 | Teoh et al. |
| 2007/0149982 A1 | | 6/2007 | Lyons |
| 2007/0172506 A1 | | 7/2007 | Nycz et al. |
| 2007/0173846 A1 | | 7/2007 | Bharadwaj et al. |
| 2007/0173852 A1 | | 7/2007 | Gil et al. |
| 2007/0173880 A1 | | 7/2007 | Nycz et al. |
| 2007/0191873 A1 | | 8/2007 | Bharadwaj et al. |

* cited by examiner

*Primary Examiner* — Ellen C Hammond

(57) ABSTRACT

A surgical procedure and a device used in the procedure according to which one end portion of a guide rod is inserted into the condyle of a damaged area of a human. The rod is used as a guide for a drill bit and a chisel to cut an opening in the condyle.

20 Claims, 8 Drawing Sheets

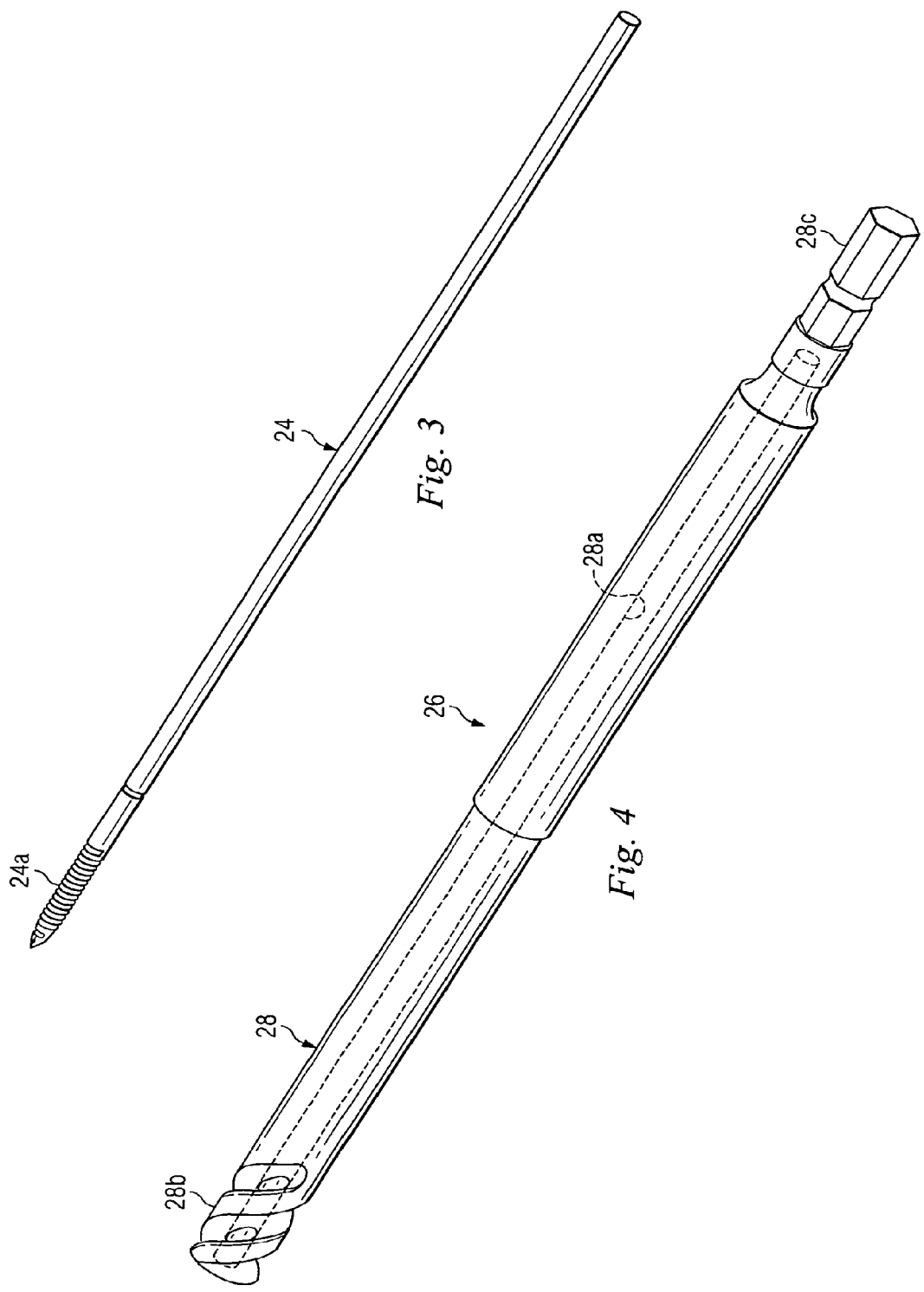

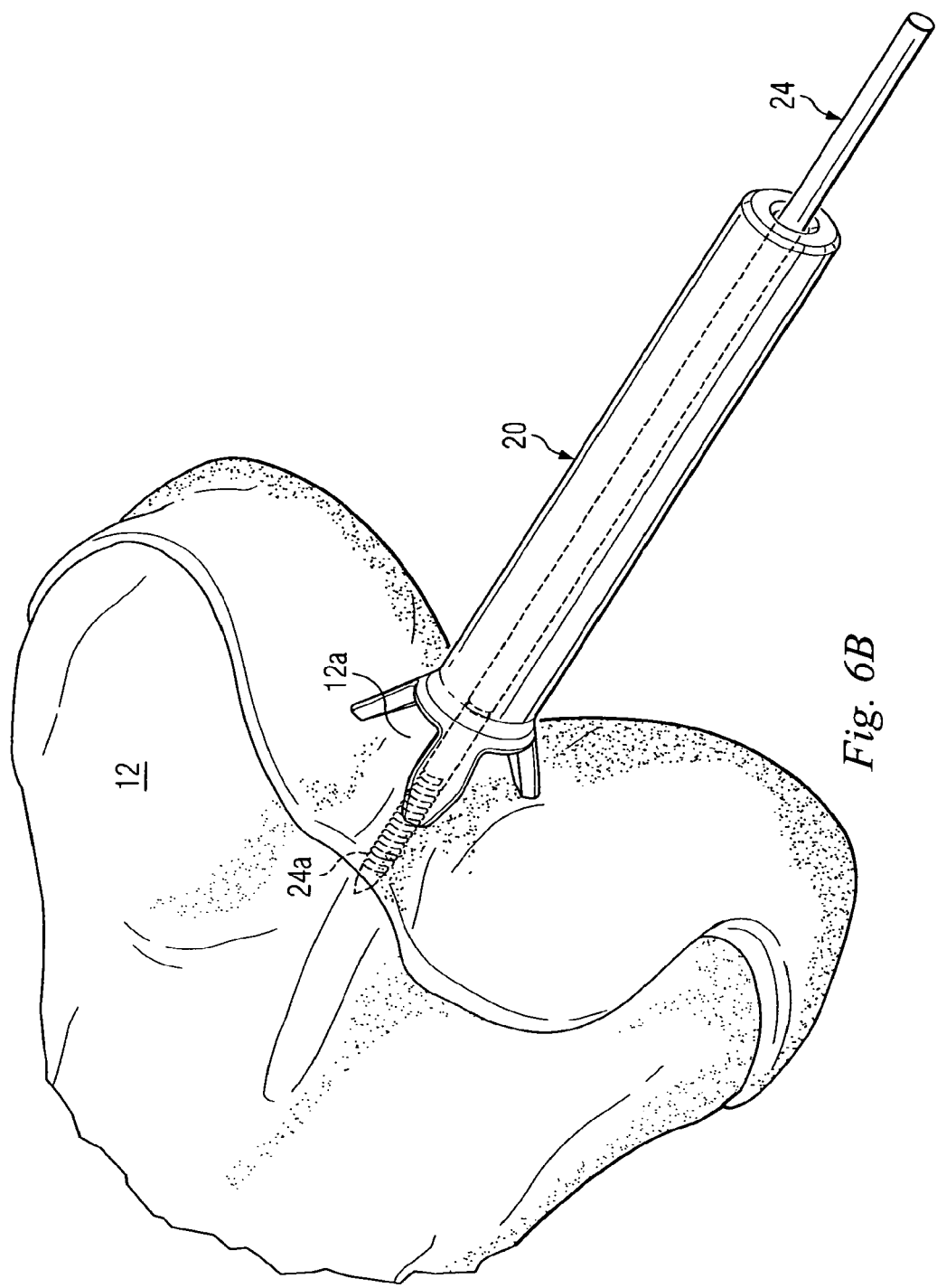

OSTEOCHONDRAL IMPLANT FIXATION METHOD

CROSS-REFERENCE TO RELATED APPLICATIONS

This application is a divisional of U.S. patent application Ser. No. 11/340,884, filed Jan. 27, 2006, the entirety of which is incorporated by reference.

BACKGROUND

This invention relates to an improved osteochondral implant fixation method and, more particularly, to such a method in which a recipient opening is prepared for receiving a graft.

In the human body, the knee consists of three articulating components—a femur, a tibia, and a patella—that are held in place by various ligaments. The corresponding chondral areas of the femur and the tibia form a hinge joint, and the patella protects the joint. Portions of the latter areas, as well as the underside of the patella, are covered with an articular cartilage, which allow the femur and the tibia to smoothly glide against each other without causing damage.

The articular cartilage often tears, usually due to traumatic injury (often seen in athletics) and degenerative processes (seen in older patients). This tearing does not heal well due to the lack of nerves, blood vessels and lymphatic systems; and the resultant knee pain, swelling and limited motion of the bone(s) must be addressed.

Damaged adult cartilages have historically been treated by a variety of surgical interventions including lavage, arthroscopic debridement, and repair stimulation, all of which provide less than optimum results.

Another known treatment involves removal and replacement of the damaged cartilage with a prosthetic device. However, the known artificial prostheses have largely been unsuccessful since they are deficient in the elastic, and therefore in the shock-absorbing, properties characteristic of the cartilage. Moreover, the known artificial devices have not proven able to withstand the forces inherent to routine knee joint function.

In an attempt to overcome the problems associated with the above techniques, osteochondral transplantation, also known as "mosaicplasty" or "OATS" has been used to repair articular cartilages. This procedure involves removing injured tissue from the articular defect and drilling cylindrical openings in the base of the defect and underlying bone. Cylindrical plugs, consisting of healthy cartilage overlying bone, are obtained from another area of the patient, typically from a lower weight-bearing region of the joint under repair, or from a donor patient, and are implanted in the openings. However, in these cases, if the opening is too large, the graft can rotate in the opening and become loose, which will prevent integration with the surrounding tissues. If the opening is too small, significant cellular damage can occur to the graft during the implantation.

Co-pending U.S. patent application Ser. No. 11/120,136, filed Apr. 30, 2005, addresses the above problems with cylindrical grafts by disclosing a implanting technique involving grafts including at least one bone portion having a cross-sectional profile other than that of a circle and including a mechanical stop to resist rotation. The disclosure of this application is hereby incorporated by reference.

An embodiment of the present invention involves a technique for providing an opening in the defect having dimensions corresponding to those of the grafts disclosed in the above application.

BRIEF DESCRIPTION OF THE DRAWING

FIG. 3 is an isometric view of a guide rod used in the procedure.

FIG. 4 is an isometric view of a drill bit used in the procedure.

FIG. 6B is similar to that of FIG. 6A but depicts the guide rod of FIG. 3 extending through the tripod.

DETAILED DESCRIPTION

Figure 1:
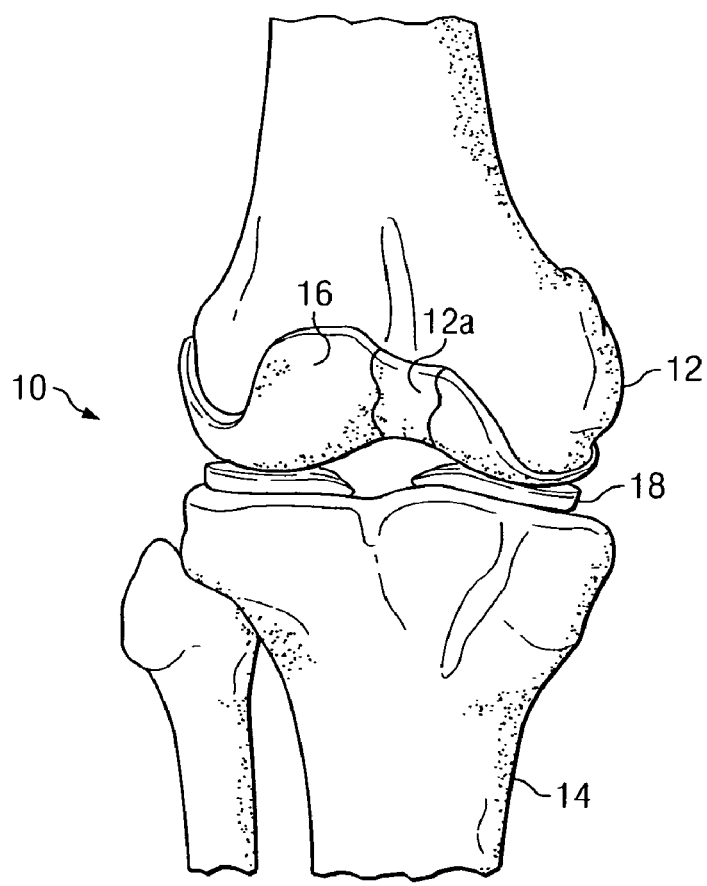
FIG. 1 is an elevational view of a human knee with certain parts removed in the interest of clarity.

Referring to FIG. 1 of the drawing, the reference numeral 10 refers, in general, to a knee area of a human including a femur 12 and a tibia 14 whose respective chondral areas are in close proximity. A cartilage 16 extends over a portion of the chondral area of the femur 12, and a meniscus 18 extends between the cartilage and the tibia 14. The patella, as well as the tendons, ligaments, and quadriceps that also form part of the knee are not shown in the interest of clarity.

It will be assumed that a portion of the cartilage 16 extending over a chondral area 12a of the femur 12 has been damaged and removed by the surgeon, or has worn away, and it is desired to create an opening in the damaged area, or defect, to receive a graft. It will also be assumed that a graft having a square cross section is harvested or prepared from another area of the patient/recipient, or from any number of anatomic sites, animal or otherwise, in accordance with the disclosure of the above patent application.

Figure 2:
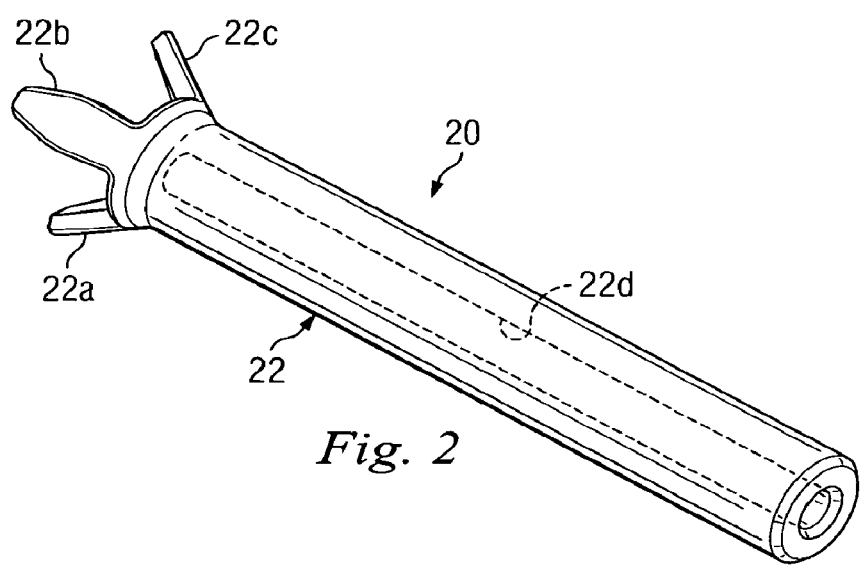
FIG. 2 is an isometric view of a tripod used in a procedure according to an embodiment of the invention.

Referring to FIG. 2, a tripod 20 is provided that consists of an elongated tubular body member 22 having three legs 22a, 22b, and 22c, each extending downwardly from one end of the body member and at an angle to its axis. The legs 20a, 20b, and 20c can be formed integrally with the body member 22 or can be fabricated separately and attached to the body member in any conventional manner. A bore 22d extends through the entire length of the body member 22.

A guide rod 24 is shown in FIG. 3 and is in the form of an elongated solid cylinder having a threaded end portion 24a.

Referring to FIG. 4, a drill bit 26 is provided that consists of a body member 28 having a continuous bore 28a. A helical cutting thread 28b is formed on the outer surface of one end portion of the body member 28, and the other end portion has a reduced-diameter solid portion 28c having a hexagonal cross section for receiving a chuck (not shown).

Figure 5:
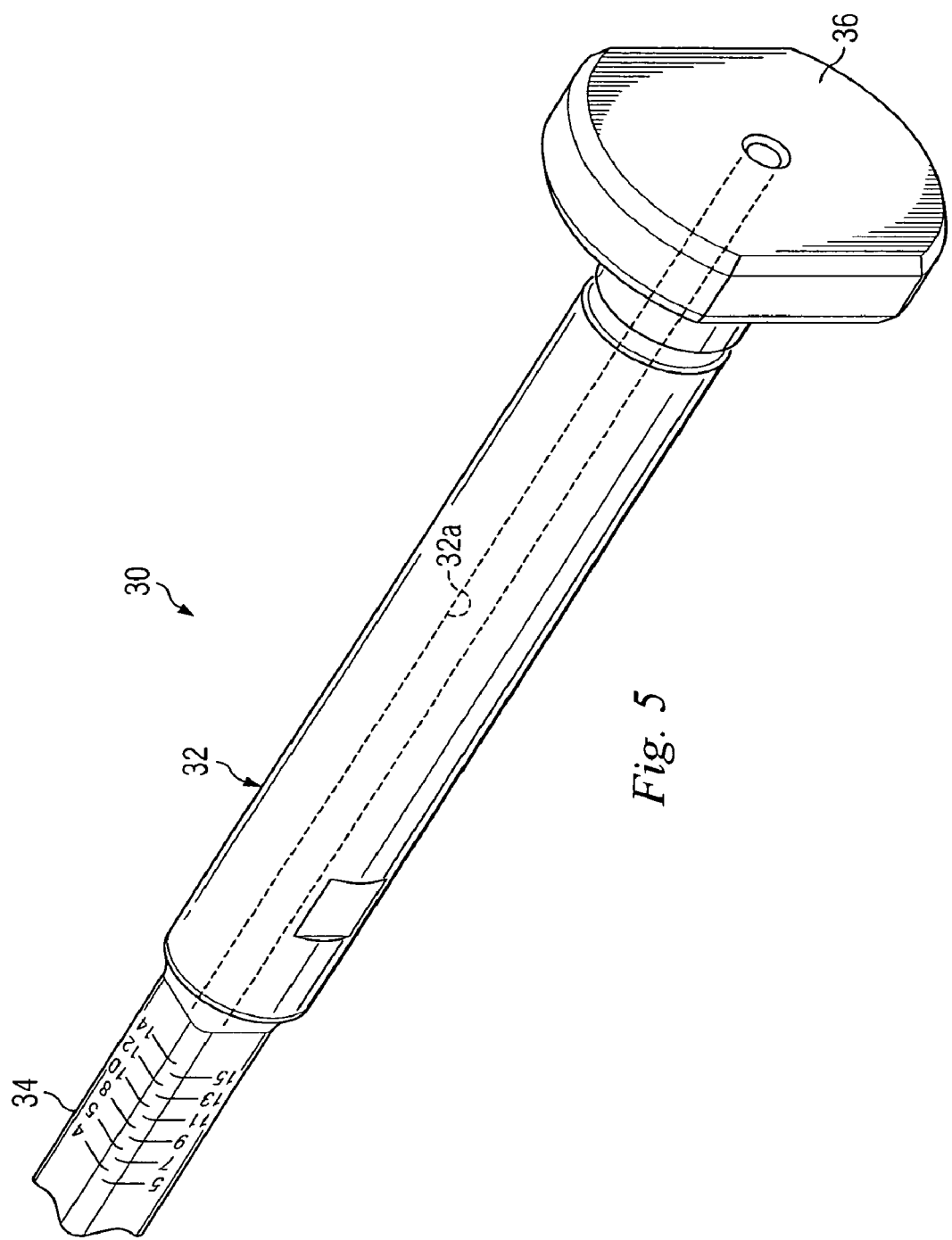
FIG. 5 is an isometric view of a chisel used in the procedure.

A cutting device, or chisel, 30 is shown in FIG. 5 and includes a body member 32 having a continuous bore 32a. A hollow cutting blade 34, having a rectangular cross section, is provided at one end of the body member, and a handle 36 is provided on the other end. Indicia are formed on the outer surface of the blade 34 for reasons to be described.

Figure 6A:
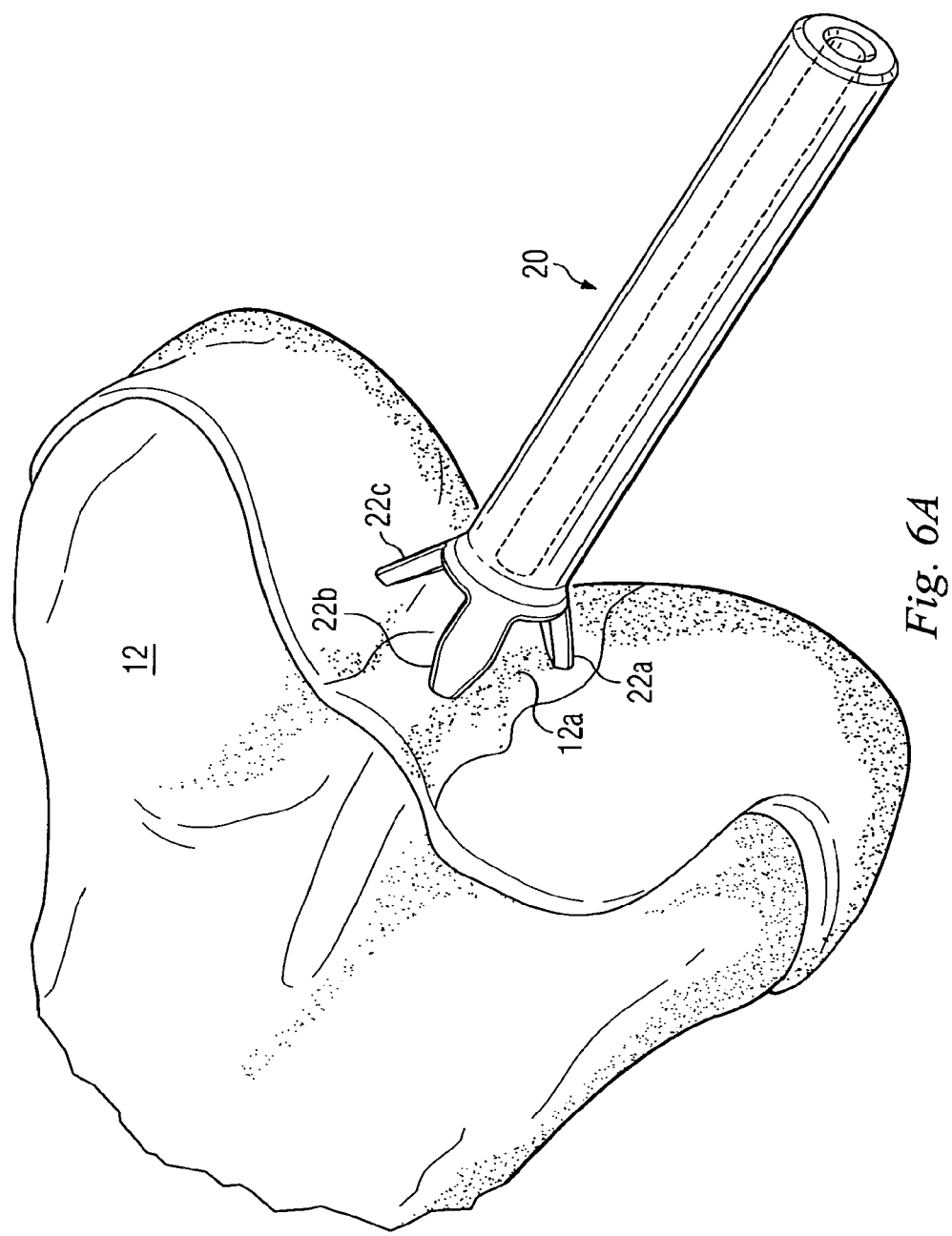
FIG. 6A depicts the tripod of FIG. 2 extending over a portion of the femur of FIG. 1.

According to the procedure, and with reference to FIG. 6A, the portion of the damaged area, or defect, 12a that is to receive the graft is marked using a sterile pen, and the tripod 20 is placed over the mark, with the legs 22a-22c engaging the corresponding surfaces of the femur 12 around the mark. A guide mark is made on the guide rod 24 a predetermined distance from the end of its threaded end portion, with the distance from the mark to the latter end corresponding to the desired depth of the guide rod insertion.

As shown in FIG. 6B, the end portion 24a of the guide rod 24 is then inserted into and through the bore 22d in the tripod 20 until it engages the mark on the defect 12a. The other end portion of the guide rod 24 projects outwardly from the corresponding end of the tripod 20 which receives a chuck (not shown) of a hand or electric drill. Torque is applied to the rod 24 to drive its threaded end portion 24a into the condyle of the femur 12 until the marked portion of the rod extents flush with the chondral area of the defect 12a. The tripod 10 is then removed, leaving the guide rod 24 implanted in the condyle and extending perpendicularly to the chondral area.

Figure 6C:
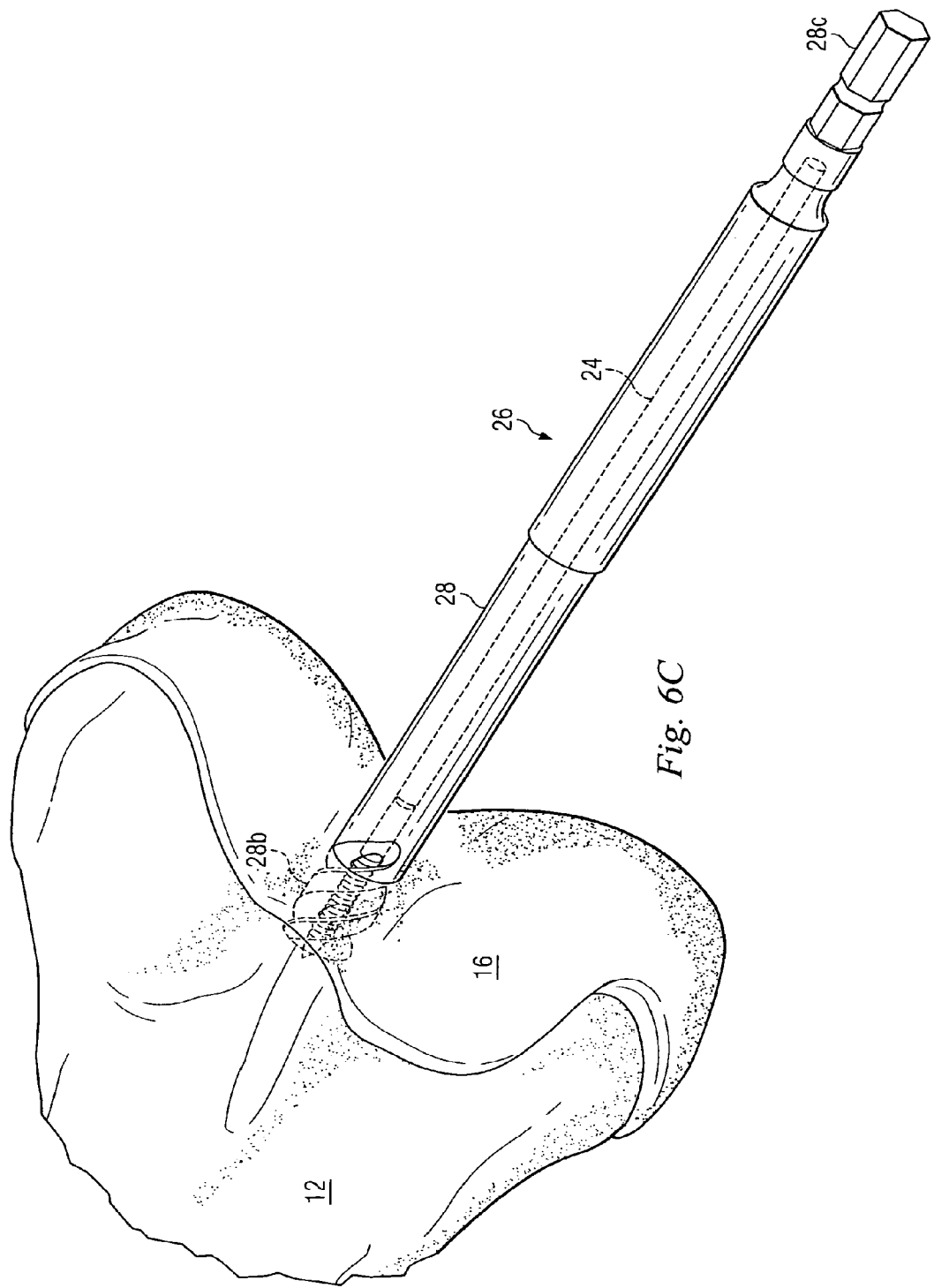
FIG. 6C is similar to that of FIG. 6B but depicting the tripod removed and the drill bit of FIG. 4 extending over the guide rod.
Figure 6D:
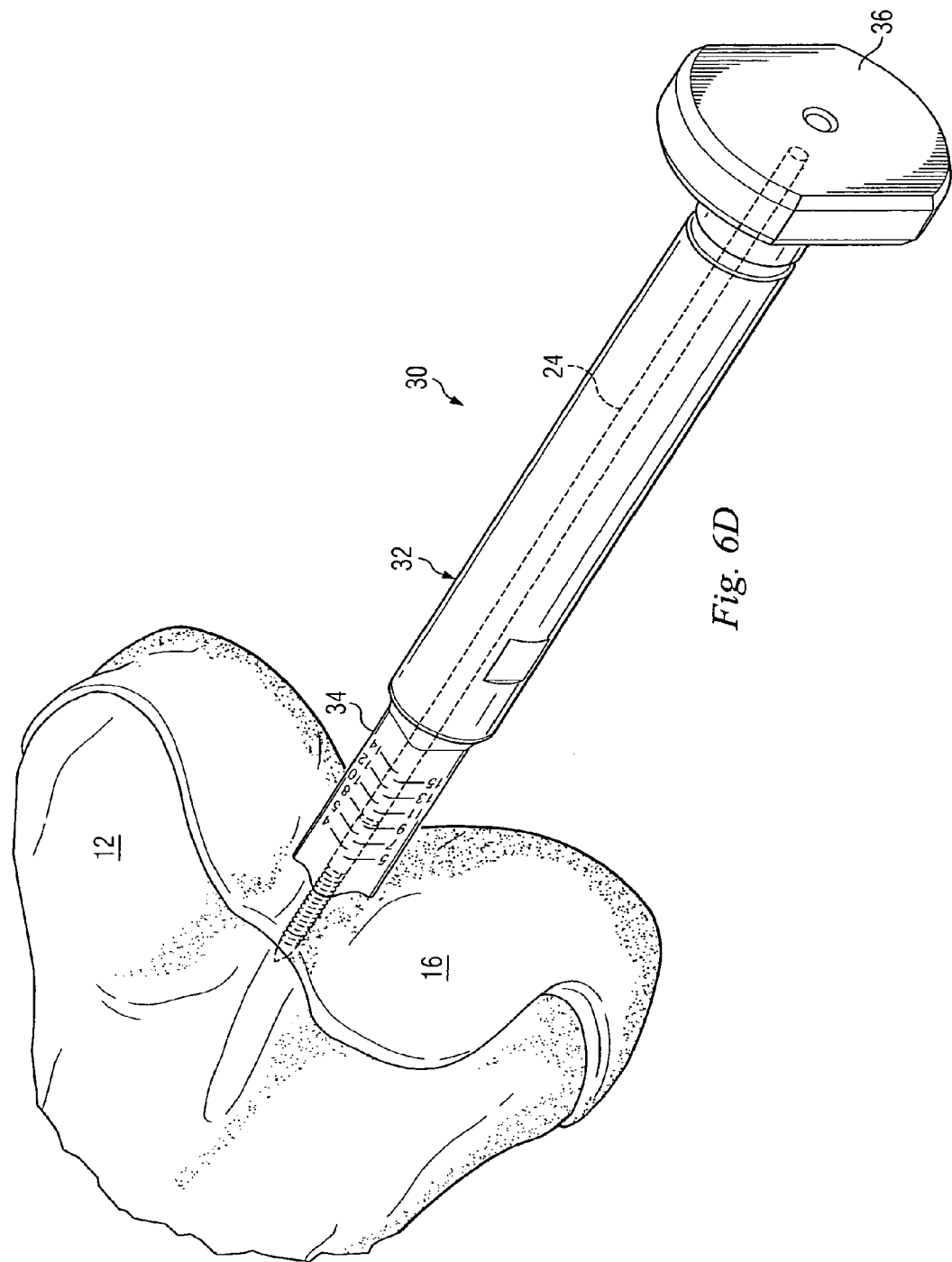
FIG. 6D is similar to that of FIG. 6C, but depicting the chisel of FIG. 5 extending over the guide rod.

Referring to FIG. 6C, the drill bit 26 is advanced over the rod until the end of the cutting thread 28b engages the chondral area of the defect 12a. A mark is made on the cutting thread 28b of the drill bit 26 that extends a distance from the corresponding end of the drill bit corresponding to the desired depth of the opening to be formed in the defect 12a. In the event that some of the damaged cartilage 16 remains, then the end of the cutting thread 28b would initially be rested on its upper surface. The other end portion 28c of the body member 28 is engaged by a chuck (not shown) of a hand or electric drill. Then the drill is activated at a relatively low RPM with very little manual pressure until the cutting thread 26b fully penetrates any of the cartilage 16 remaining on the chondral area of the defect 12a. The pressure on the bit 26 is then increased so that the cutting thread 28b starts cutting the subchondral condyle. This continues until the marked portion of the cutting thread 28b extends flush with the chondral area of the defect 12a. Thus, an opening having a circular cross-section is formed in the defect 12a and extends to the desired, predetermined depth.

The bit 26 is removed from the rod 24 and the chisel 30 is advanced over the rod until the end of the cutting blade 34 engages the chondral area of the defect 12a. Then, manual force is applied to the chisel 30 so that the blade expands the opening cut by the bit 26 into an opening 12b having a rectangular cross section corresponding to the cross-section of the blade.

It is understood that a dilator, or the like (not shown) can be inserted in the opening 12b to smooth out the walls of the opening as necessary and expand the opening a relatively small amount as necessary to permit insertion of the graft. A dialator of this type is shown in co-pending application No. filed Jan. 26, 2006, the disclosure of which is hereby incorporated by reference.

Figure 7:
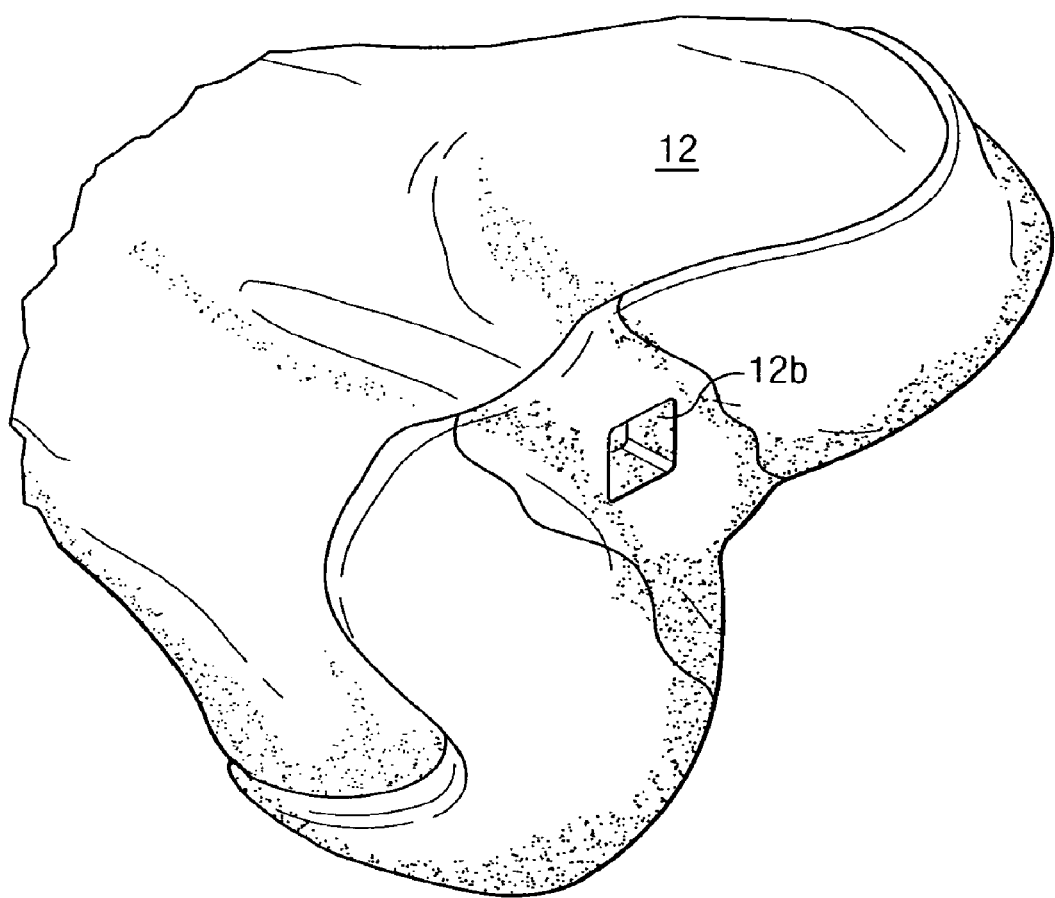
FIG. 7 depicts the femur of FIG. 1 with the opening made in accordance with the procedure.

The opening 12b is shown in FIG. 7, extends perpendicularly to the chondral area, and is adapted to receive a graft (not shown) of a corresponding size.

It is understood that, during the above procedure, any of the meniscus 18 or related tendons, ligaments and quadriceps are removed or pushed aside as necessary to permit access to the defect 12a to permit the forming of the opening 12b.

VARIATIONS

1. The shape and dimensions of the opening 12b can vary within the scope of the invention. For example, the opening can be circular or have just one planar surface.

2. The guide rod 24 can be hammered into the condyle using a light hammer.

3. The spatial references mentioned above, such as "upper", "lower", "under", "over", "between", "outer", "inner" and "surrounding" are for the purpose of illustration only and do not limit the specific orientation or location of the components described above.

4. The present invention is not limited to knees of humans but rather is applicable other damaged areas of all animals.

5. The graft 20 can be harvested or prepared from another area of the patient/recipient, or from any number of anatomic sites, animal or otherwise 6. The method and device disclosed above can be used in any surgical or experimental situation (animal species or otherwise) to create prepared recipient sites in any anatomic region containing cartilage or bone.

7. The opening formed in accordance with the above can accept a cartilage or bone substitute material.

8. The opening 12b can be adapted using appropriately shaped reamers, curettes, press-fit expanders or dilators, or other general surgical instruments.

9. Should the defect be sufficiently large to not be completely resurfaced using one graft, this procedure can be repeated with one or more additional openings and grafts adjacent to the opening 12b.

10. The tripod in the above embodiment can be replaced by similar manual/visual instruments to achieve similar perpendicularity.

Those skilled in the art will readily appreciate that many other variations and modifications of the embodiment described above without materially departing from the novel teachings and advantages of this invention. Accordingly, all such variations and modifications are intended to be included within the scope of this invention as defined in the following claims. In the claims, means-plus-function clauses are intended to cover the structures described herein as performing the recited function and not only structural equivalents, but also equivalent structures.

What is claimed is:

1. A surgical system comprising:
    a hollow drill bit having a circular cross section configured to form an opening in tissue having a circular cross section;
    a bone chisel having a body member having a proximal end and a distal end with a continuous bore for receiving a guide rod between the proximal and distal ends, a hollow cutting blade having a rectangular cross section at the proximal end and a handle at the distal end, the cutting blade having a proximal end defining a proximal face having four sides, each of the sides having an arcuate configuration so as to expand the opening having a circular cross section into an opening having a rectangular cross section when force is exerted on the cutting blade;
    a guide rod; and
    a tripod having an open bore through the tripod configured to receive the guide rod and three legs spaced apart from one another each having a tip configured to engage tissue.

2. The surgical system of claim 1, wherein the bone chisel comprises indicia on an outer surface of the hollow cutting blade.

3. The surgical system of claim 2, wherein the tripod comprises an elongated tubular body member and the three legs each extend downwardly from one end of the body member and at an angle to its axis.

4. The surgical system of claim 3, wherein the guide rod comprises an elongated solid cylinder having a threaded end portion.

5. The surgical system of claim 2, wherein the guide rod comprises an elongated solid cylinder having a threaded end portion.

6. The surgical system of claim 1, wherein the tripod comprises an elongated tubular body member and the three legs each extend downwardly from one end of the body member and at an angle to its axis.

7. The surgical system of claim 6, wherein the guide rod comprises an elongated solid cylinder having a threaded end portion.

8. The surgical system of claim 1, wherein the guide rod comprises an elongated solid cylinder having a threaded end portion.

9. The surgical system of claim 1, wherein the tripod comprises an elongated tubular body member and the three legs each extend downwardly from one end of the body member of the tripod, each of the legs having a pair of convexly curved side surfaces extending between the one end of the body member of the tripod and the tip of each leg.

10. The surgical system of claim 1, wherein the tripod comprises an elongated tubular body member extending between a proximal end and a distal end, the three legs each extending downwardly from the proximal end of the body member of the tripod, the body member of the tripod having a uniform diameter between the proximal end of the body member of the tripod and the distal end of the body member of the tripod.

11. The surgical system of claim 1, wherein the tripod comprises an elongated tubular body member extending between a proximal end and a distal end defining a distal face, the body member of the tripod being tapered between the distal end of the body member of the tripod and the distal face.

12. The surgical system of claim 1, wherein the body member of the bone chisel is an elongated tubular body and the rectangular cutting blade extends from the proximal end of the body member.

13. The surgical system of claim 1, wherein the body member of the bone chisel is an elongated tubular body having a first width and the rectangular cutting blade extends from the proximal end of the body member and has a second with that is less than the first width, the bone chisel having a tapered portion between the proximal end of the body member and the rectangular cutting blade.

14. The surgical system of claim 1, wherein the body member of the bone chisel is an elongated tubular body having a first width and the rectangular cutting blade extends from the proximal end of the body member and has a second with that is less than the first width, the bone chisel having a tapered portion between the proximal end of the body member and the rectangular cutting blade including an outer surface that is smooth.

15. The surgical system of claim 1, wherein the handle of the bone chisel has a disc-shaped configuration and includes a planar distal face.

16. The surgical system of claim 1, wherein the guide rod comprises an elongated solid cylinder having a threaded end portion, the guide rod including a guide mark a predetermined distance from the threaded end portion corresponding to a desired depth of insertion for the guide rod.

17. The surgical system of claim 1, wherein the guide rod comprises an elongated solid cylinder having a threaded end portion, the threaded end portion being tapered between a distal cylindrical portion and a pointed proximal tip.

18. The surgical system of claim 1, wherein the drill bit comprises a body member extending between a distal end and a proximal end, the body member of the drill bit including an outer surface having a helical cutting thread at the proximal end of the body member of the drill bit, the distal end of the body member of the drill bit having a reduced-diameter solid portion having a hexagonal cross section for receiving a chuck.

19. The surgical system of claim 1, wherein the guide rod is configured for disposal within the bore of the chisel, within the bore of the tripod and within the hollow drill bit.

20. The surgical system of claim 1, wherein the guide rod has an outer surface and a first width, the chisel has an inner surface defining the bore of the chisel and the tripod has an inner surface defining the bore of the tripod, the bore of the chisel and the bore of the tripod each having a second width that is greater than the first width such that the outer surface of the guide rod engages the inner surface of the chisel when the guide rod is disposed within the bore of the chisel and the outer surface of the guide rod engages the inner surface of the tripod when the guide rod is disposed within the bore of the tripod.

* * * * *